(12) United States Patent
Suchanek et al.

(10) Patent No.: US 8,975,424 B1
(45) Date of Patent: Mar. 10, 2015

(54) ZINC-PROMOTED CATALYSTS FOR EPOXIDATION OF ETHYLENE

(71) Applicant: Scientific Design Company, Inc., Little Ferry, NJ (US)

(72) Inventors: Wojciech Suchanek, Wyckoff, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/143,684

(22) Filed: Dec. 30, 2013

(51) Int. Cl.
*C07D 301/10* (2006.01)
*B01J 23/66* (2006.01)

(52) U.S. Cl.
CPC ............. *B01J 23/66* (2013.01); *C07D 301/10* (2013.01)
USPC ........................................................ 549/536

(58) Field of Classification Search
CPC .................................................... C07D 301/10
USPC ........................................................ 549/536
See application file for complete search history.

(56) References Cited

U.S. PATENT DOCUMENTS

| | | |
|---|---|---|
| 3,563,914 A | 2/1971 | Wattmena |
| 3,702,259 A | 11/1972 | Nielsen |
| 4,007,135 A | 2/1977 | Hayden et al. |
| 4,226,782 A | 10/1980 | Hayden et al. |
| 4,242,235 A | 12/1980 | Cognion et al. |
| 4,761,394 A | 8/1988 | Lauritzen |
| 4,766,105 A | 8/1988 | Lauritzen |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,112,795 A | 5/1992 | Minahan et al. |
| 5,187,140 A | 2/1993 | Thorsteinson et al. |
| 5,266,548 A | 11/1993 | Koradia et al. |
| 5,380,697 A | 1/1995 | Matusz et al. |
| 5,407,888 A | 4/1995 | Herzog et al. |
| 5,502,020 A * | 3/1996 | Iwakura et al. ............... 502/317 |
| 5,597,773 A | 1/1997 | Evans et al. |
| 5,831,037 A | 11/1998 | Ohsuga et al. |
| 6,153,556 A * | 11/2000 | Shima et al. ................... 502/348 |
| 6,831,037 B2 | 12/2004 | Szymanski et al. |
| 2004/0110973 A1 | 6/2004 | Matusz |
| 2005/0096219 A1 | 5/2005 | Szymanski et al. |
| 2012/0264953 A1 | 10/2012 | Rosendahl et al. |

FOREIGN PATENT DOCUMENTS

RU 2177829 * 1/2002
WO WO2012140616 A1 10/2012

OTHER PUBLICATIONS

Drake, L.C., et al., "Macropore-Size Distributions in Some Typical Porous Substances", Ind. Eng. Chem. Anal. Ed., Publication Date: Dec. 1945, 17 (12), pp. 787-791.
Brunauer, S., et al., "Adsorption of Gases in Multimolecular Layers", J. Am. Chem. Soc., Feb. 1938, pp. 309-316.

* cited by examiner

*Primary Examiner* — Taofiq A Solola
(74) *Attorney, Agent, or Firm* — Scully, Scott, Murphy & Presser, P.C.

(57) ABSTRACT

A silver-based ethylene oxide catalyst is provided that has enhanced stability. The enhanced stability is obtained in the present invention by providing a silver-based ethylene oxide catalyst that includes from 100 ppm to 1000 ppm of zinc, and from greater than 450 ppm to less than 800 ppm of cesium. Zinc and cesium are promoters that are introduced to a finished carrier either prior to, coincidentally with, or subsequent to the deposition of the silver. The silver-based ethylene oxide catalyst can be used in the epoxidation of ethylene to ethylene oxide.

18 Claims, No Drawings

ZINC-PROMOTED CATALYSTS FOR EPOXIDATION OF ETHYLENE

FIELD OF THE INVENTION

The present invention relates to silver-based ethylene oxide catalysts, and more particularly, to a zinc-promoted silver-based ethylene oxide catalyst having enhanced stability.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, but not necessarily always, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group metals (e.g., sulfur and/or halide compounds) can also be included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

It is well known that with extended use of a catalyst, the catalyst will age (i.e., degrade) to a point until use of the catalyst is no longer practical. There is thus a continuous effort to extend the useful lifetime (i.e., "longevity" or "usable life") of catalysts. The useful lifetime of the catalyst is directly dependent on the stability of the catalyst. As used herein, the "useful lifetime" is the time period for which a catalyst can be used until one or more of its functional parameters, such as selectivity or activity, degrade to such a level that use of the catalyst becomes impractical.

Stability of the catalyst has largely been attributed to various characteristics of the carrier. Some characteristics of the carrier that have undergone much research include carrier formulation, surface area, porosity, and pore volume distribution, among others.

The most widely used formulation for the carriers of ethylene epoxidation catalysts are those based on alumina, typically alpha-alumina. Much research has been directed to investigating the effect of the alumina composition for improving stability and other properties of the catalyst. The preparation and modification of alumina carriers for enhancing ethylene epoxidation catalyst performance are described, for example, in U.S. Pat. Nos. 4,226,782, 4,242,235, 5,266,548, 5,380,697, 5,597,773, 5,831,037 and 6,831,037 as well as in U.S. Patent Application Publication Nos. 2004/0110973 A1 and 2005/0096219 A1.

Despite the above, there remains a need in the art for further improvements in the stability of ethylene epoxidation catalysts which are not based upon the carrier formulation. There is a particular need for improving the stability of such catalysts by means that are facile and financially feasible.

SUMMARY OF THE INVENTION

A silver-based ethylene oxide catalyst is provided that has high selectivity as well as enhanced stability. The silver-based ethylene oxide catalyst of the present invention may also be referred to herein as an ethylene epoxidation catalyst. Applicants have determined that when zinc and cesium promoters are both used in the promoting amounts specified in the present application, a silver-based ethylene oxide catalyst can be produced that has a combination of high selectivity and long-term stability. Notably, high selectivity and enhanced stability is obtained in the present invention by providing a silver-based ethylene oxide catalyst that includes from 100 ppm to 1000 ppm of zinc and from greater than 450 ppm to less than 800 ppm of cesium. Zinc and cesium are promoters that are introduced to a finished carrier either prior to, coincidentally with, or subsequent to the deposition of silver. The silver-based ethylene oxide catalyst can be used in the epoxidation of ethylene to ethylene oxide.

In one aspect of the present invention, an ethylene epoxidation catalyst is provided that comprises a carrier; a catalytic amount of silver deposited on and/or in the carrier; from 100 ppm to 1000 ppm of zinc deposited on and/or in the carrier; and from greater than 450 ppm to less than 800 ppm of cesium deposited on and/or in the carrier.

Another aspect of the present invention relates to a method of forming an epoxidation catalyst. The method of the present invention comprises depositing a catalytic amount of silver, from 100 ppm to 1000 ppm of zinc and from greater than 450 ppm to less than 800 ppm of cesium on and/or in a carrier, wherein the depositing of zinc and cesium occurs either prior to, coincidentally with, or subsequent to the depositing of silver; and subjecting the carrier containing silver, zinc and cesium to a calcination process.

A yet further aspect of the present invention relates to a process for the vapor phase conversion of ethylene to ethylene oxide in the presence of oxygen. The process of the present invention comprises providing an ethylene epoxidation catalyst to an ethylene oxide reactor, wherein the ethylene epoxidation catalyst comprises a carrier, a catalytic amount of silver deposited on and/or in the carrier, from 100 ppm to 1000 ppm of zinc deposited on and/or in the carrier, and from greater than 450 ppm to less than 800 ppm of cesium deposited on and/or in the carrier; and reacting a reaction mixture comprising ethylene and oxygen in the present of the ethylene epoxidation catalyst.

DETAILED DESCRIPTION OF THE INVENTION

The present invention provides an enhanced stability silver-based ethylene epoxidation catalyst that includes from 100 ppm to 1000 ppm of zinc and from greater than 450 ppm to less than 800 ppm of cesium. Zinc and cesium are promoters that are introduced to a finished carrier either prior to, coincidentally with, or subsequent to the deposition of the silver. By "finished carrier" it is meant a carrier that has been subjected to a carrier firing process. By "enhanced stability" it is meant that the silver-based ethylene epoxidation catalyst of the present invention has longer usable lifetimes, and particularly, a significantly reduced degradation in selectivity as compared to an equivalent catalyst which does not include zinc and cesium promoters in the ranges mentioned above, over equivalent time periods of usage. Throughout the present application, various elements from the Periodic Table of Elements are defined utilizing the IUPAC nomenclature.

The carrier that can be employed in the present invention may be selected from a large number of solid supports which may be porous or nonporous. The carriers are relatively inert to the epoxidation feedstock materials, products and reaction conditions for the intended use, such as for the epoxidation of an olefin. The carrier that can be employed may be a refractory inorganic material such as, for example, alumina-, silica- or titania-based compounds, or combinations thereof such as alumina-silica carriers.

In one embodiment, the carrier is an alumina carrier. The alumina carrier that can be employed in the present invention is composed of any of the refractory alumina compositions known in the art for use in ethylene oxidation catalysts. In one embodiment of the present invention, the carrier that is employed includes alpha-alumina as the alumina component. In some embodiments of the present invention, the alpha-alumina used in the present invention has a high purity, i.e., about 80 weight % or more, and more typically, 95 weight % or more alpha-alumina. In other embodiments of the present invention, the alpha-alumina carrier that can be employed in the present invention may have a purity that is below 80 weight %. Remaining components of the alumina carrier that can be used in the present invention may be other phases of alumina, silica, mullite, alkali metal oxides and trace amounts of other metal-containing and/or non-metal-containing additives or impurities. The remaining components that are present in the aluminum carrier of the present invention are below promoters amounts (to be defined herein below).

When an alumina carrier is employed, the alumina carrier is typically porous and, in one embodiment, has a B.E.T. surface area of at most 20 $m^2/g$. In another embodiment, the B.E.T. surface area of the alumina carrier can be in the range from 0.1 $m^2/g$ to 10 $m^2/g$. In yet another embodiment of the present invention, the alumina carrier that can be employed may have a B.E.T. surface area from 0.2 $m^2/g$ to 3 $m^2/g$. In a further embodiment, the alumina carrier that can be employed in the present invention can be characterized by having a B.E.T. surface area from 0.3 $m^2/g$ to 3 $m^2/g$, preferably from 0.5 $m^2/g$ to 2.5 $m^2/g$, and more preferably from 0.6 $m^2/g$ to 2.0 $m^2/g$. The B.E.T. surface area described herein can be measured by any suitable method, but is more preferably obtained by the method described in Brunauer, S., et al., *J. Am. Chem. Soc.*, 60, 309-16 (1938).

In one embodiment, the alumina carrier that can be employed in the present invention may have a water absorption value ranging from 0.2 cc/g to 0.8 cc/g. In another embodiment, the alumina carrier that can be employed in the present invention may have a water absorption value ranging from 0.25 cc/g to 0.6 cc/g.

The alumina carrier that can be employed in the present invention can have any suitable distribution of pore diameters. As used herein, the "pore diameter" is used interchangeably with "pore size". In one embodiment, the pore diameters can be at least 0.01 microns (0.01 μm). In another embodiment, the pore diameters can be at least 0.1 μm. In different embodiments, the pore diameters can be at least 0.5 μm, or 0.8 μm. Typically, the pore diameters are no more than 50 μm.

The alumina carrier that can be employed in the present invention can be monomodal or multimodal such as, for example, bimodal. Without wishing to be bound by any theory, it is believed that a catalyst with a multimodal pore size distribution possesses a type of pore structure in which reaction chambers are separated by diffusion channels.

In one embodiment, at least 40% of the pore volume of the alumina carrier can be attributable to pores with diameters between 1 micrometer and 5 micrometers. In another embodiment, at least 60% of the pore volume of the alumina carrier can be attributable to pores with diameters between 1 micrometer and 5 micrometers. In yet a further embodiment, at least 80% of the pore volume of the alumina carrier can be attributable to pores with diameters between 1 micrometer and 5 micrometers.

In one embodiment, the median pore diameter of the alumina carrier employed is between 1 micrometer and 5 micrometers. In another embodiment, the median pore diameter of the carrier employed is between 1 micrometer and 4.5 micrometers. In yet another embodiment, the median pore diameter of the alumina carrier employed is between 1 micrometer and 4 micrometers. In a further embodiment of the present invention, the medium pore diameter of the alumina carrier employed can be greater than 15 microns. In one example, the medium pore diameter of the alumina carrier can be between 17 microns and 25 microns. In some embodiments of the present invention, the pore volume from pores with a diameter of 5 micrometers and above is typically less than 0.20 ml/g, more typically less than 0.10 ml/g, and even more typically less than 0.05 ml/g. In some embodiments of the present invention, the pore volume from pores with a diameter of 1 micrometer and less is typically less than 0.20 ml/g, and more typically less than 0.16 ml/g.

In some embodiments, the water pore volume of the alumina carrier can be from 0.10 cc/g to 0.80 cc/g. In other embodiments, the water pore volume of the alumina carrier can be from 0.20 cc/g to 0.60 cc/g. The pore volume and pore size distribution of the carrier described herein can be measured by any suitable method, but are more preferably obtained by the conventional mercury intrusion porosimetry method as described in, for example, Drake and Ritter, "Ind. Eng. Chem. Anal. Ed.," 17, 787 (1945).

The carrier that can be employed in the present invention can be prepared utilizing procedures well known in the art. Alternatively, the carrier that can be employed in the present invention is commercially available. For example, suitable alumina carriers are manufactured and generally commercially available, for example from the NorPro Company of Akron, Ohio.

In one embodiment and for example, an alumina carrier can be made by mixing a high-purity aluminum oxide, such as, for example, alpha-alumina, with temporary and permanent binders. The temporary binders, that include burnout materials, are thermally decomposable organic compounds of moderate to high molecular weight which, on decomposition, enhance the pore structure of the carrier. The temporary binders are essentially removed during firing when producing the final carrier. Some examples of burnout materials include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of an alumina carrier.

The permanent binders are typically inorganic clay-type materials having fusion temperatures below that of the alumina, such as silica, aluminum, calcium or magnesium silicates with one or more alkali metal compounds. Optionally a transitional alumina can be present. The permanent binders typically impart mechanical strength to the finished carrier.

After thorough dry-mixing, sufficient water and/or other suitable liquid is added to help form the mass into a paste-like substance. Carrier particles are formed from the paste by conventional means, such as extrusion. After molding into the desired shape, the carrier particles can be calcined at a temperature from 1200° C. to 1600° C. to form the support, i.e., carrier. When the particles are formed by extrusion, it may be desirable to also include extrusion aids. The amounts of extrusion aids required depend on a number of factors that relate to the equipment used. Such factors are well within the general knowledge of a person skilled in the art of extruding ceramic materials.

The carrier that can be employed in the present invention can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors. In one embodiment, the carrier particles typically have equivalent diameters in the range of from 3 mm to 12 mm, and more typically in the range of from 5 mm to 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

In some embodiments of the present invention, the carrier, e.g., alpha alumina carrier, that can be employed in the present invention has an initial low alkali metal content. By "low alkali metal content" it is meant that the carrier contains from 2000 ppm or less, typically from 30 ppm to 300 ppm, of alkali metal therein. Carriers containing low alkali metal content can be obtained utilizing techniques that are well known in the art. For example, and in one embodiment, substantially no alkali metal(s) is(are) used during the carrier manufacturing process. By "substantially no alkali metal" it is meant that only trace amounts of alkali metal are used during the carrier manufacture process. In another embodiment, a carrier having a low alkali metal content can be obtained by performing various washing steps to the carrier precursor materials used in forming the carrier. The washing steps can include washing in water, a base or an acid.

In other embodiments of the present invention, the carrier that can be used has an alkali metal content that is above the value mentioned above for the carrier having the low alkali metal content. In such an embodiment the carrier that can be employed in the present invention typically contains a measurable level of sodium on the surface thereof. The concentration of sodium at the surface of the carrier will vary depending on the level of sodium within the different components of the carrier as well as the details of its calcination. In one embodiment of the present invention, the carrier that can be employed in the present invention has a surface sodium content of from 5 ppm to 200 ppm, relative to the total mass of the carrier. In another embodiment of the present invention, the carrier that can be employed in the present invention has a surface sodium content of from 7 ppm to 70 ppm, relative to the total mass of the carrier. The sodium content mentioned above represents that which is found at the surface of the carrier and that which can be leached, i.e., removed, by de-ionized water.

In order to produce the catalyst of the present invention, a carrier having the above characteristics is then provided with a catalytically effective amount of silver thereon and/or therein. The catalyst can be prepared by impregnating the carrier with silver ions, compounds, complexes, and/or salts dissolved in a suitable solvent sufficient to cause deposition of silver precursor compound onto and/or into the carrier. In some embodiments of the present invention, and as will be described in greater detail herein below, the carrier can be simultaneously impregnated and incorporated with silver, zinc and cesium, along with any additional desired promoter or additional promoter combination, by any of the conventional methods known in the art, e.g., by excess solution impregnation, incipient wetness impregnation, spray coating, and the like. Typically, the carrier material is placed in contact with the silver-containing solution until a sufficient amount of the solution is absorbed by the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for catalyst deposition by impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. The complexing/solubilizing agent may be present in the impregnating solution in an amount from about 0.1 to about 10 moles of ethylene diamine per mole of silver, preferably from about 0.5 to about 5 moles, and more preferably from about 1 to about 4 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

In addition to silver, the catalyst of the present invention further includes zinc and cesium as main promoters; other additional promoters as known in the art and described herein below can also be used in the present invention besides zinc and cesium.

The zinc and cesium promoters can be incorporated into the carrier either prior to, coincidentally with, or subsequent to the deposition of the silver. Typically, the zinc and cesium promoters are incorporated into the carrier coincidentally with silver, and other additional promoters (to be described in greater detail herein below).

In accordance with an embodiment of the present invention, an enhanced stability silver-based ethylene oxide catalyst can be obtained when from 100 ppm to 1000 ppm of zinc and from greater than 450 ppm to less than 800 ppm of cesium are deposited on and/or in the carrier. In accordance with another embodiment of the present invention, an enhanced stability silver-based ethylene oxide catalyst can be obtained when from 200 ppm to 800 ppm of zinc and from 550 ppm to 750 ppm of cesium are deposited on and/or in the carrier. In accordance with yet another embodiment of the present invention, an enhanced stability silver-based ethylene oxide catalyst can be obtained when from 400 ppm to 600 ppm of zinc and from 625 ppm to 725 ppm of cesium are deposited on and/or in the carrier.

Applicants have determined that when zinc and cesium promoters are both used in the promoting amounts specified in the present application, a silver-based ethylene oxide catalyst can be produced that has a combination of high selectivity and long-term stability. When the amounts of zinc and/or cesium are outside the ranges described above, a silver-based ethylene oxide catalyst can be obtained, but the stability is less than that of the silver-based ethylene oxide catalyst of the present application.

As stated above and in one embodiment of the present invention, the zinc promoter and/or the cesium promoter is (are) added to the carrier in the amounts specified above prior to adding silver to the carrier. In another embodiment of the present invention, the zinc promoter and/or the cesium promoter is (are) added to the carrier in the amounts specified above at the same time as silver. In yet another embodiment of the present invention, the zinc promoter and/or the cesium promoter is (are) added in the amounts specified above to the carrier after silver addition. In some embodiments of the present invention, zinc and silver, but not necessarily cesium and the other additional promoters, are co-deposited onto the carrier.

The zinc promoter that can be used in the present invention includes at least one zinc salt that is soluble in a solution that is used for depositing the zinc promoter on the carrier. The solution that is used to deposit the zinc promoter may include one of the solvents mentioned above for depositing silver on the carrier. In one example, the solution that is used to deposit the zinc promoter is an aqueous solution. Examples of zinc salts that can be used in the present invention include a zinc halide, zinc sulfate, zinc nitrate, zinc carboxylate and mixtures thereof. In one example, zinc nitrate is used as the zinc promoter.

The cesium promoter that can be used in the present invention includes at least one cesium salt that is soluble in a solution that is used for depositing the zinc promoter on the carrier. The solution that is used to deposit the cesium promoter may include one of the solvents mentioned above for depositing silver on the carrier. In one example, the solution that is used to deposit the cesium promoter is an aqueous solution. Examples of cesium salts that can be used in the present invention include a cesium halide, cesium sulfate, cesium nitrate, cesium nitrile, cesium carboxylate and mixtures thereof. In one example, cesium nitrate is used as the cesium promoter.

In addition to zinc and cesium, any one or more additional promoting species in a promoting amount can also be incorporated into the carrier either prior to, coincidentally with, or subsequent to the deposition of the silver, zinc and cesium. As used herein, a "promoting amount" of a certain component refers to an amount of that component that works effectively to provide an improvement in one or more of the catalytic properties of a subsequently formed catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, catalysts of the present invention may include a promoting amount of an additional alkali metal other than cesium or a mixture of two or more additional alkali metals other than cesium. Suitable additional alkali metal promoters include, for example, lithium, sodium, potassium, rubidium, or combinations thereof. Thus, and in one example, a silver-based ethylene oxide catalyst including silver, zinc, cesium and one of lithium, sodium, potassium and rubidium can be provided in the present invention. The amount of additional alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the additional alkali metal.

The catalyst of the present invention may also include a promoting amount of a Group 2 alkaline earth metal or a mixture of two or more Group 2 alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The catalyst of the present invention may also include a promoting amount of a main group element or a mixture of two or more main group elements. Suitable main group elements include any of the elements in Groups 13 (boron group) to 17 (halogen group) of the Periodic Table of the Elements. For example, the carrier can include a promoting amount of one or more sulfur compounds, one or more phosphorus compounds, one or more boron compounds, one or more halogen-containing compounds, or combinations thereof. The carrier can also include a main group element, aside from the halogens, in its elemental form.

The catalyst of the present invention may also include a promoting amount of an additional transition metal other than zinc or a mixture of two or more additional transition metals other than zinc. Suitable additional transition metals other than zinc can include, for example, the elements from Groups 3 (scandium group), 4 (titanium group), 5 (vanadium group), 6 (chromium group), 7 (manganese group), 8-10 (iron, cobalt, nickel groups), and 11 (copper group) of the Periodic Table of the Elements, as well as combinations thereof. More typically, the additional transition metal is an early transition metal selected from Groups 3, 4, 5, 6, or 7 of the Periodic Table of Elements, such as, for example, hafnium, yttrium, molybdenum, tungsten, rhenium, chromium, titanium, zirconium, vanadium, tantalum, niobium, or a combination thereof.

In one embodiment of the present invention, the enhanced stability catalyst of the present invention includes silver, cesium, zinc and rhenium. In another embodiment of the present invention, the enhanced stability catalyst of the present invention includes silver, cesium, zinc, rhenium and one or more species selected from K, Li, W and S. In a further embodiment of the present invention, the enhanced stability catalyst of the present invention includes silver, cesium, zinc, rhenium and one or more species selected from Li and S.

The catalyst of the present invention may also include a promoting amount of a rare earth metal or a mixture of two or more rare earth metals. The rare earth metals include any of the elements having an atomic number of 57-71, yttrium (Y) and scandium (Sc). Some examples of these elements include lanthanum (La), cerium (Ce), and samarium (Sm).

The additional transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of these promoters, aside from the alkali metals, can be in any suitable form, including, for example, as zerovalent metals or higher valent metal ions.

After impregnation with silver, zinc, cesium and any additional promoters, the impregnated carrier is removed from the solution and calcined for a time sufficient to reduce the silver component to metallic silver and to remove volatile decomposition products from the silver-containing carrier. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated carriers. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose.

During calcination, the impregnated carrier is typically exposed to a gas atmosphere comprising air or an inert gas, such as nitrogen. The inert gas may also include a reducing agent.

In another aspect, the present invention is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. A typical process for the oxidation of ethylene to ethylene oxide comprises the vapor phase oxidation of ethylene with molecular oxygen in the presence of the catalyst of the present invention in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The catalysts of the present invention have been shown to be particularly selective catalysts in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the catalyst of the present invention broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or byproducts, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-350 kg EO per cubic meters of catalyst per hour. More typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

Examples have been set forth below for the purpose of further illustrating the present invention. The scope of the present invention is not to be in any way limited by the examples set forth herein.

Silver Stock Solution for silver-based ethylene oxide catalyst: 277.5 g of deionized water was placed in cooling bath to maintain temperature during the whole preparation under 50° C. At continuous stirring, 221.9 g of ethylenediamine was added in small portions to avoid overheating. 174.1 g of oxalic acid dihydrate was then added to the water-ethylenediamine solution in small portions. After all oxalic acid was dissolved, 326.5 g of high purity silver oxide was added to solution in small portions. After all silver oxide was dissolved and the solution was cooled to about 35° C. it was removed from the cooling bath. After filtration, the solution contained roughly 30 wt % silver, and had a specific gravity of 1.55 g/mL.

In the examples to follow, each silver-based ethylene oxide catalyst employed a conventional alpha-alumina carrier having a surface area of 0.64 $m^2$/gm, and a water absorption of 44%. The conventional alpha-alumina carrier that was employed in each instance was bimodal containing a first mode between ~5 microns, and a second mode around ~1 micron. The carrier also had 12% of pores having a pore size of less than 1 micron, 2.3% of pores having a pore size of less than 0.5 microns and 0% of pores having a pore size of less than 0.2 microns. The carrier was washed prior to introducing silver and the other promoters to the carrier.

Catalyst Preparation: A 150 g portion of the above mentioned carrier was placed in a flask and evacuated to about 0.1 torr prior to impregnation. To the above silver stock solution were added aqueous solutions of cesium as cesium hydroxide, zinc as zinc nitrate, and one or more other promoters in various forms, including rhenium as ammonium per-rhenate, in sufficient concentrations to prepare a catalyst composition having the amount of zinc and cesium promoters as specified in Table 1. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was done on a moving belt calciner. In this unit, the wet catalyst was transported on a stainless steel belt through a multi-zone furnace. All zones of the furnace were continuously purged with pre-heated, ultra-high purity nitrogen and the temperature was increased gradually as the catalyst passes from one zone to the next. The heat was radiated from the furnace walls and from the pre-heated nitrogen. The wet catalyst entered the furnace at ambient temperature. The temperature in the catalyst layer was then increased gradually to a maximum of about 400° C. as the catalyst passed through the heated zones. In the last (cooling) zone, the temperature of the now activated silver-based ethylene oxide catalyst was immediately lowered to less than 100° C. before it emerged into ambient atmosphere. The total residence time in the furnace was approximately 45 minutes.

EXAMPLE 1

This example investigates the effects that a zinc promoter has on catalyst selectivity and stability. Notably, silver-based ethylene oxide catalysts as described in Table 1 were prepared using the catalyst preparation described above. The silver-based ethylene oxide catalysts described in Table 1 contain substantially the same amounts of silver, cesium, and additional one or more promoters (concentrations 10 ppm-900 ppm), but different amounts of zinc promoter (i.e., from 0 to 500 ppm). The catalyst including no zinc promoter was prepared utilizing the same procedure as mentioned above except no zinc was provided to the silver stock solution; the non-zinc promoted catalyst was used as a base line and for comparison in the present example. After calcination, micro-reactor test was performed on each of the catalysts shown in Table 1. Specifically, the tests were performed with conditioning at ΔEO=2.2 mol %, with the following feed composition: $[C_2H_4]$=15%, $[O_2]$=7%, $[CO_2]$=2%, and $N_2$ balance gas. The results of the micro-reactor tests for each of the catalysts investigated in this example are also shown in Table 1.

TABLE 1

Summary of compositions and performances in micro-reactor tests of silver-based ethylene oxide catalysts with and without zinc promoter

| Catalyst No. | [Zn] ppm | [Ag] Wt % | [Cs] ppm | Selectivity decline rate, ΔS/Δt (selectivity points per month) |
|---|---|---|---|---|
| 1 | 0 | 17.0 | 692 | 10.6 |
| 2 | 82 | 16.7 | 682 | 10.0 |

TABLE 1-continued

Summary of compositions and performances in micro-reactor tests of silver-based ethylene oxide catalysts with and without zinc promoter

| Catalyst No. | [Zn] ppm | [Ag] Wt % | [Cs] ppm | Selectivity decline rate, ΔS/Δt (selectivity points per month) |
|---|---|---|---|---|
| 3 | 168 | 16.7 | 681 | 4.0 |
| 4 | 253 | 16.7 | 678 | 0.7 |
| 5 | 419 | 16.7 | 680 | 2.3 |
| 6 | ~500 | 16.9 | 706 | 0.0 |

From the above results, it was observed that adding 82 ppm Zn into a catalyst composition, results in certain reduction of selectivity and no stability improvement. However, when [Zn] increases above 82 ppm the catalysts exhibit significantly improved stability (ΔS/Δt=0.0-4.0 sel. points/month as compared to 10.6 for non-zinc containing silver-based ethylene oxide catalyst) and higher activity (5-10° C.). With increasing [Zn], selectivity does not drop below the 87% level of high selectivity catalysts but the stability improves. As [Zn] exceeds 250 ppm, its effects seem to reach a plateau at about ΔS/Δt=0.0-2.3 sel. points/month. It can be thus concluded that Zn used as promoter significantly enhances stability and activity of the silver-based high selectivity catalysts (HSC).

EXAMPLE 2

This example investigates the effects that a cesium promoter has on zinc promoted silver-based ethylene oxide catalysts containing 500 ppm zinc and amounts of cesium varying between 300 ppm and 800 ppm. The catalysts compositions were prepared on the alpha-alumina carrier described above. Notably, a first silver-based catalyst containing 500 ppm zinc and 327 ppm cesium (outside the claimed invention), a second silver-based catalyst containing 500 ppm zinc and 675 ppm cesium (in accordance with the present invention) and a third silver-based catalyst containing 500 ppm zinc and 825 ppm cesium (outside the claimed invention were prepared). The content of silver in each instance was about 17 wt %. Each catalyst also included one or more other promoters, with concentrations ranging from 10 ppm to 900 ppm.

Micro-reactor tests were performed on each of the above mentioned catalysts. The tests were performed with conditioning at ΔEO=2.2 mol %, with the following feed composition: $[C_2H_4]$=15%, $[O_2]$=7%, $[CO_2]$=2%, and $N_2$ balance gas.

At low [Cs]=327 ppm, the catalyst was active but had low selectivity of about 84%. Increasing [Cs] to 675 ppm increased the selectivity to 87-88%. Such catalyst was also very stable, as reported earlier (ΔS/Δt=0.0-0.7 sel. points/month). At high [Cs] of 826 ppm, the catalyst had very low activity and the selectivity quickly dropped below the 80% level. These results demonstrate the importance of using a zinc-promoted silver-based ethylene oxide catalyst that has a cesium content that is within the range recited in the present application.

While the present invention has been particularly shown and described with respect to various embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An ethylene epoxidation catalyst comprising:
   a carrier;
   a catalytic amount of silver deposited on and/or in said carrier;
   a promoting amount of rhenium deposited on and/or in said carrier;
   from 100 ppm to 1000 ppm of zinc deposited on and/or in said carrier; and
   from greater than 450 ppm to less than 800 ppm of cesium deposited on and/or in said carrier.

2. The ethylene epoxidation catalyst of claim 1, wherein the carrier comprises alumina, charcoal, pumice, magnesia, zirconia, titania, kieselguhr, fuller's earth, silicon carbide, silica, silicon dioxide, magnesia, clays, artificial zeolites, natural zeolites, ceramics or combinations thereof.

3. The ethylene epoxidation catalyst of claim 1, wherein the carrier comprises alpha-alumina.

4. The ethylene epoxidation catalyst of claim 1, further comprising a promoting amount of one or more additional promoters, wherein said one or more additional promoters is selected from the group consisting of Group 2 alkali earth metal promoters, one or more transition metals comprising a metal selected from Group 3-11 of the Periodic Table of Elements, one or more alkali metals and any combination thereof.

5. The ethylene epoxidation catalyst of claim 4, wherein said one or more transition metals comprise a metal selected from the group consisting of Groups 3, 4, 5, and 7 of the Periodic Table of the Elements.

6. The ethylene epoxidation catalyst of claim 5, wherein said one or more transition metals is selected from the group consisting of molybdenum, tungsten, chromium, titanium, hafnium, zirconium, vanadium, thorium, tantalum, and niobium.

7. The ethylene epoxidation catalyst of claim 5, wherein said one or more transition metals comprise molybdenum, tungsten, or any combination thereof.

8. The ethylene epoxidation catalyst of claim 4, wherein said one or more alkali metals is selected from the group consisting of lithium, sodium, potassium, and rubidium.

9. The ethylene epoxidation catalyst of claim 8, wherein said one or more alkali metals is lithium.

10. The ethylene epoxidation catalyst of claim 1, further comprising a promoting amount of one or more additional promoters, wherein said one or more additional promoters is selected from the group consisting of one or more sulfur-containing compounds, one or more fluorine-containing compounds, one or more phosphorus-containing compounds and any combination thereof.

11. The ethylene epoxidation catalyst of claim 1, wherein from 250 ppm to 700 ppm of said zinc is deposited on and/or in said carrier.

12. The ethylene epoxidation catalyst of claim 1, wherein from 600 ppm to 750 ppm of said cesium is deposited on and/or in said carrier.

13. A method of forming an ethylene epoxidation catalyst, said method comprising;
   depositing a catalytic amount of silver, a promoting amount of rhenium, from 100 ppm to 1000 ppm of zinc and from greater than 450 ppm to less than 800 ppm of cesium on and/or in a carrier, wherein said depositing said zinc, said rhenium and said cesium occurs either prior to, simultaneously with, or subsequent to said depositing said silver; and
   subjecting said carrier containing said silver, said zinc, said rhenium and said cesium to a calcination process.

14. The method of claim 13, further comprising depositing a promoter amount of additional promoters to said carrier, wherein said one or more additional promoters is selected from the group consisting of Group 2 alkali earth metal promoters, one or more transition metals comprising a metal selected from Group 3-11 of the Periodic Table of Elements, one or more alkali metals and any combination thereof, and said depositing of said additional promoters occurs either prior to, simultaneously with, or subsequent to said depositing said silver.

15. The method of claim 13, further comprising depositing a promoter amount of additional promoters to said carrier, wherein said one or more additional promoters is selected from the group consisting of one or more sulfur-containing compounds, one or more fluorine-containing compounds, one or more phosphorus-containing compounds and any combination thereof, and said depositing of said additional promoters occurs either prior to, simultaneously with, or subsequent to said depositing said silver.

16. The method of claim 13, wherein from 250 ppm to 700 ppm of said zinc is deposited on and/or in said carrier.

17. The method of claim 13, wherein from 600 ppm to 750 ppm of said cesium is deposited on and/or in said carrier.

18. A process for the vapor phase conversion of ethylene to ethylene oxide in the presence of oxygen, said process comprising:
   providing an ethylene epoxidation catalyst to an ethylene oxide reactor, wherein said ethylene epoxidation catalyst comprises a carrier, a catalytic amount of silver deposited on and/or in said carrier, a promoting amount of rhenium, from 100 ppm to 1000 ppm of zinc deposited on and/or in said carrier, and from greater than 450 ppm to less than 800 ppm of cesium deposited on and/or in said carrier; and
   reacting a reaction mixture comprising ethylene and oxygen in the present of said ethylene epoxidation catalyst.

* * * * *